United States Patent
Hirsch et al.

[11] 4,212,201
[45] Jul. 15, 1980

[54] ULTRASONIC SENSOR

[75] Inventors: John M. Hirsch; Robert G. Stapleton, both of Houston, Tex.

[73] Assignee: Shell Oil Company, Houston, Tex.

[21] Appl. No.: 936,153

[22] Filed: Aug. 23, 1978

[51] Int. Cl.² .................................... G01N 29/02
[52] U.S. Cl. ............................. 73/290 V; 73/579
[58] Field of Search ............. 73/290 V, 579, 596, 73/597, 19, 61 R

[56] References Cited
U.S. PATENT DOCUMENTS

| | | | |
|---|---|---|---|
| 3,952,578 | 4/1976 | Jacobs | 73/597 |
| 4,015,464 | 4/1977 | Miller et al. | 73/61 R |
| 4,080,837 | 3/1978 | Alexander | 73/597 |
| 4,138,879 | 2/1979 | Liebermann | 73/61 R |

Primary Examiner—Anthony V. Ciarlante

[57] ABSTRACT

A method and apparatus for identifying the fluid in a vessel, such as, a storage tank or pipeline using ultrasonic techniques. The method uses a transducer to project ultrasonic energy through the vessel and a second transducer positioned opposite the first to receive the energy that has been transmitted through the vessel and fluid. The transducers are included in a circuit whose parameters are adjusted to cause the circuit to resonate with the magnitude of the adjusted parameter being related to the fluid in the vessel.

6 Claims, 4 Drawing Figures

ULTRASONIC SENSOR

BACKGROUND OF THE INVENTION

The present invention relates to a method and apparatus using ultrasonic energy to detect the fluid in a closed vessel. The invention is particularly useful in identifying fluids flowing in a pipeline to detect interfaces between different fluids. While ultrasonic devices have been used in the past to determine fluid levels within closed vessels, they have not been used to identify the fluid in the vessel. Fluid level detection is accomplished by providing a series of transducers along the vessel and determining the fluid level by the signals from the various transducers.

BRIEF SUMMARY OF THE INVENTION

The present invention solves the problem of detecting both fluid level and the type of fluid by using a pair of ultrasonic transducers positioned opposite each other on a closed vessel. One of the transducers is used as a source to transmit ultrasonic energy through the vessel while the second transducer is used as a receiver to receive the ultrasonic energy. The transducers are coupled in series in the feedback circuit of an amplifier and produce a loss and phase shift in the circuit. The amplifier has a variable gain which may be adjusted to cause the circuit including the transducers to resonate. In particular, the gain of the amplifier is adjusted by a ramp voltage which is produced in response to a start signal. The magnitude of the ramp voltage required to cause the circuit to resonate is dependent upon the particular fluid in the closed vessel. Thus, if the time between the initiation of the ramp voltage and the onset of resonance or the time between the onset of resonance and the end of the ramp voltage is measured, it can be related directly to the fluid in the vessel.

The present invention uses a logic and clock circuit to generate both the signals for initiating the ramp voltage as well as a clock pulse which can be used to measure the time interval between the start of resonance and the end of the ramp voltage. The start of resonance is detected by comparing the output voltage of the variable gain amplifier with a reference voltage whose level is set high enough to discriminate against random noises. The detection of resonance gates on a counter which counts the clock pulses until the end of the ramp voltage. The counted pulses can be displayed visually, for example, on a light-emitting diode display and permanently recorded on suitable printing apparatus.

The measured time intervals are related directly to the fluid within the closed vessel and can be used to identify the fluids. In cases where one only desires to determine the interface between two fluids, a change in the time interval can be used to detect the interface.

BRIEF DESCRIPTION OF THE DRAWINGS

The present invention will be more easily understood from the following detailed description of a preferred embodiment in which.

PREFERRED EMBODIMENT

Figure 1:
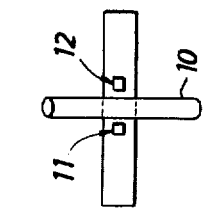
FIG. 1 is a pictorial view of the transducers mounted on a pipeline.
Figure 2:
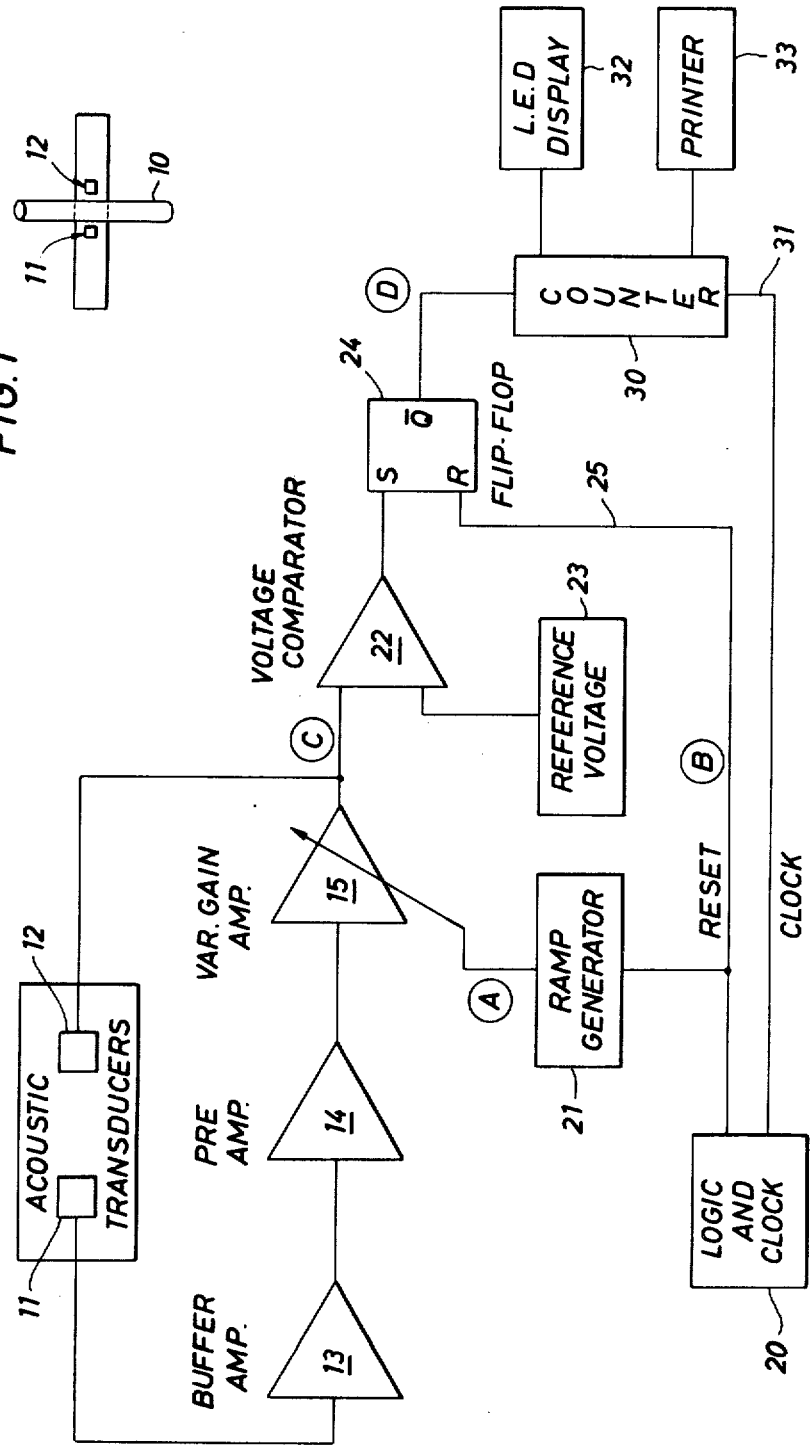
FIG. 2 is a block diagram of the electronics used for measuring the time intervals.
Figure 3:
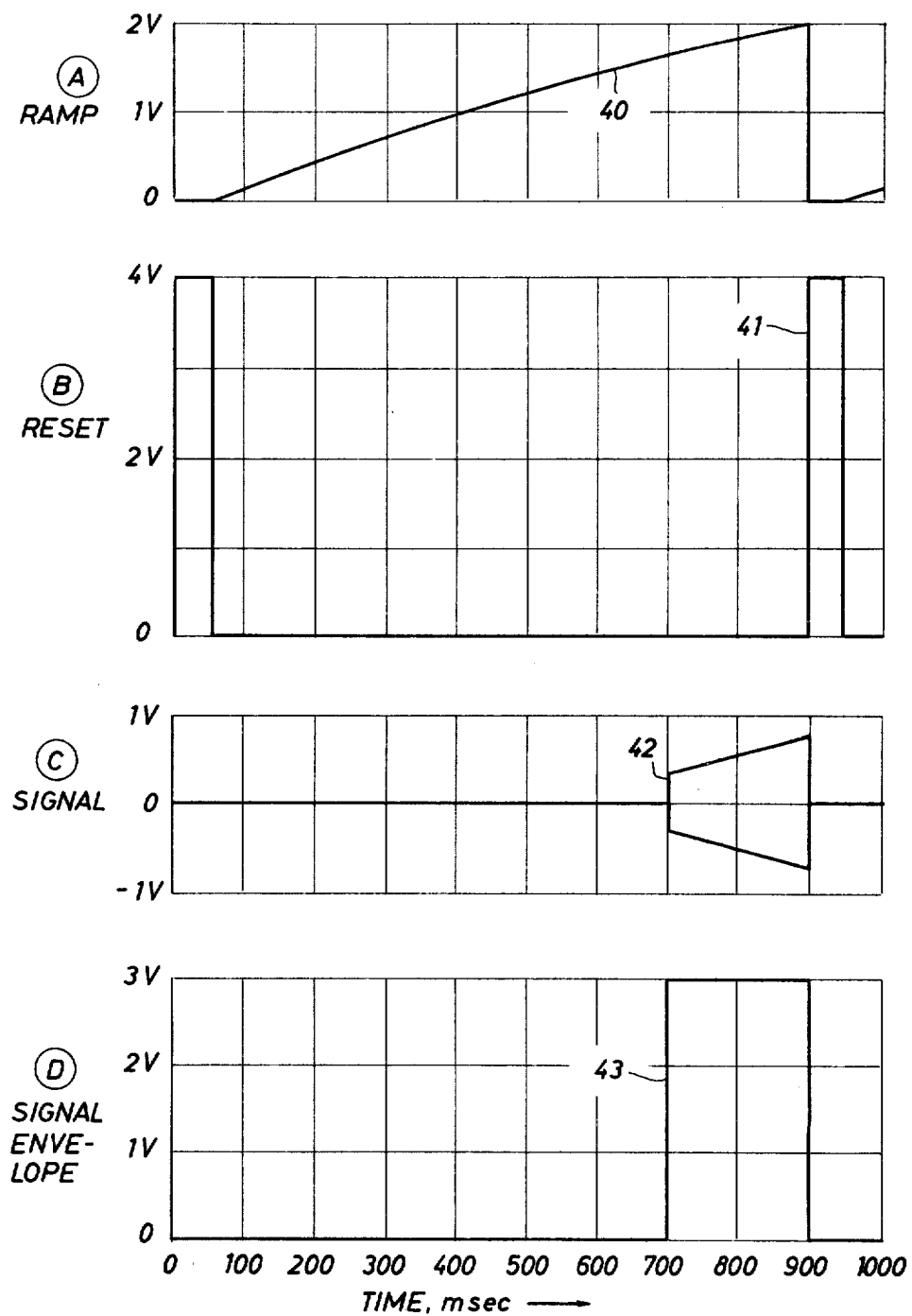
FIG. 3 is a series of wave forms present in FIG. 2.

Referring now to FIGS. 1 and 2, there are shown two transducers 11 and 12 mounted on opposite sides of a pipeline 10. The transducers should have a resonance frequency in the ultrasonic range, for example, 3 MHZ and be acoustically coupled to the walls of the pipeline. Various accoustical adhesives are available for coupling transducers to a pipeline as well as insuring that the accoustic energy from the transducer passes through the pipeline and is not dissipated in the atmosphere surrounding the pipeline. In FIG. 2, the transducers 11 and 12 are shown disposed in the feedback loop of an amplifier circuit comprising the three amplifiers 13, 14 and 15. Amplifier 15 is a variable gain amplifier whose gain is controlled by the ramp voltage described below. The logic and clock circuit 20 supplies a reset pulse shown in wave form B of FIG. 3 and a constant frequency clock signal. For example, the clock signal may have a frequency of 10 KHZ while the reset pulse may be supplied every 868 milliseconds. Obviously, various frequencies and time intervals may be used. The reset pulse is used to both initiate the generation of the ramp voltage in the voltage generator 21 and terminate the ramp voltage. The wave form of the ramp voltage is shown in the wave form A of FIG. 3 and goes from 0 level to approximately 2 volts during the 868 millisecond time interval between the reset pulses. The ramp voltage is supplied directly to the gain input of the variable gain amplifier 15. Thus, as the gain of the amplifier 15 is increased, a point will be reached at which the gain of the amplifier is sufficient to overcome the loss and phase shift caused by the combination of the transducers 11 and 12 and the fluid flowing in the pipeline 10. At this point, the output of the amplifier 15 will exceed the voltage from the reference source 23 and the voltage comparing amplifier 22 will produce an output.

The output of the amplifier 22 is used to set a flip-flop 24 which is reset by the pulse from the logic circuit supplied over the lead 25. The flip-flop 24 in turn gates on the counter 30 which counts the pulses received from the clock over the lead 31. The counter will continue to count the pulses until the ramp voltage A is returned to 0 by the reset pulse from the logic circuit. When the ramp voltage returns to 0, the output from the amplifier 15 will fall below the reference voltage and thus effectively turn off the voltage comparing circuit 22 which removes the voltage from the flip-flop. Thus, the flip-flop 24 will convert the resonant signal shown in wave form C of FIG. 3 to a square wave pulse 43 shown in wave form D of FIG. 3 for gating the counter 30. The output from the counter 30 can be either graphically displayed by means of a light-emitting diode circuit 32 or permanently recorded on a suitable printing circuit 33.

Figure 4:
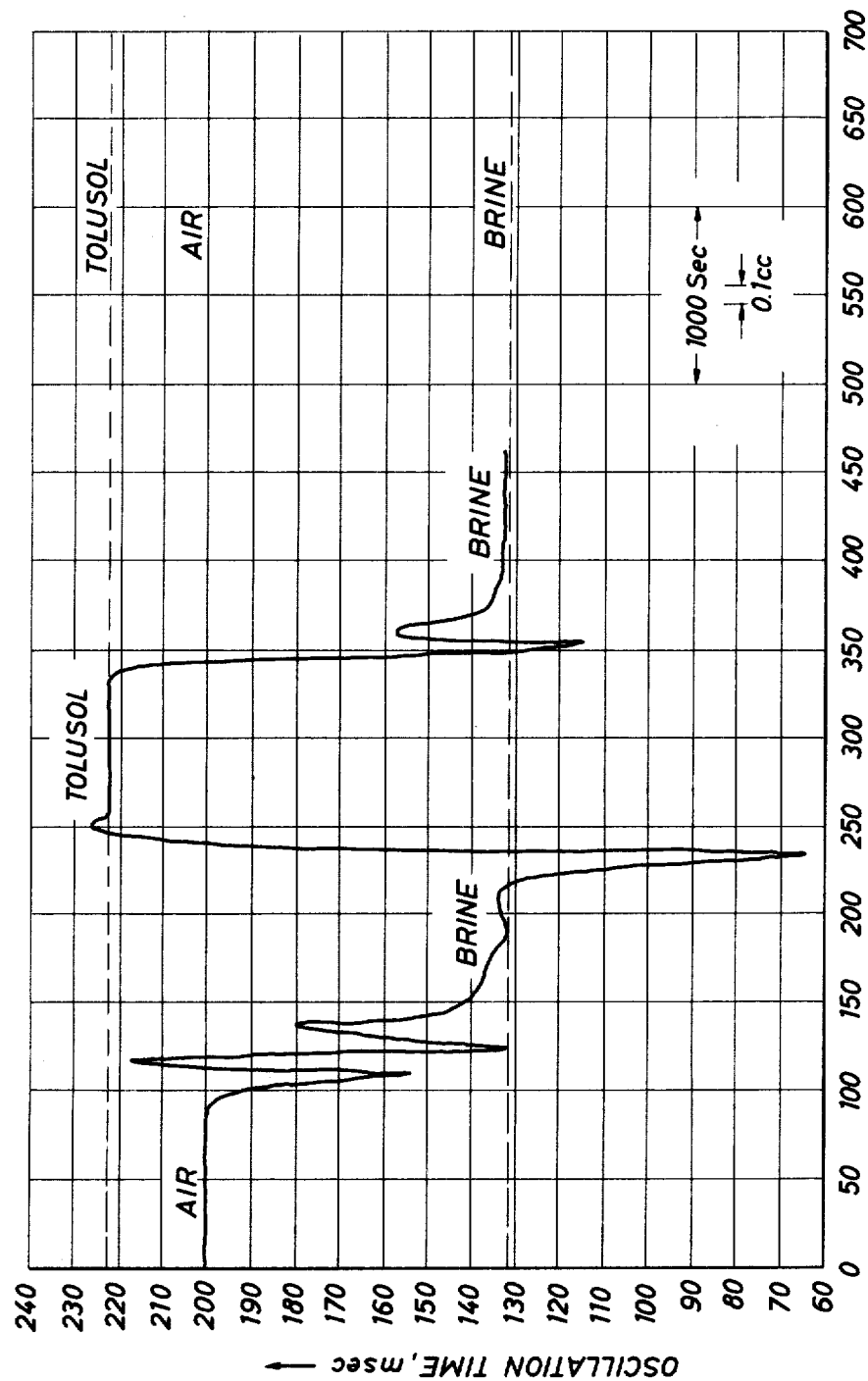
FIG. 4 is a printout of the apparatus shown in FIGS. 1 and 2 with various fluids flowing in the pipeline.

Referring now to FIG. 4, there is shown the actual time measurements obtained when the circuit described above was placed on a one-half inch outside diameter pipe having a 3/16th inch inside diameter. In addition a constant rate pump capable of circulating 0.001 cc/sec. was used to flow various immiscible fluids through the pipeline. In particular, as shown in FIG. 4, the pipeline was first dried and only air circulated through the pipeline to obtain a measurement of approximately 200 milliseconds. The air was then followed by a brine solution followed by a tolusol solution which was followed again by a brine solution. As seen from the results of FIG. 4, the brine solution produced substantially the same measurement of 135 milliseconds in both cases while the air and tolusol had considerably longer time intervals. Thus, the interface between the air and the brine and the brine and the tolusol were clearly defined.

In addition to the above data shown in FIG. 4, the data in the following table were obtained by flowing various materials through the pipeline and following each material with air. As seen, each material was run at least twice and the measured time intervals substantially agree. This permits a simple means for identifying the various materials by simply measuring the time between the onset of resonance in the end of the ramp voltage.

| Time | Fluid | Mean(msec) | Standard Deviation |
|---|---|---|---|
| 15:32 | Nujol | 7.0 | 1.1 |
| 15:40 | Air | 135.1 | 0.6 |
| 15:44 | Tolusol | 158.1 | 0.5 |
| 15:47 | Air | 134.4 | 0.8 |
| 15:54 | Kerosene | 171.3 | 0.9 |
| 15:59 | Air | 134.8 | 1.0 |
| 16:22 | Kerosene | 170.2 | 0.8 |
| 16:26 | Air | 134.1 | 0.4 |
| 16:31 | Tolusol | 157.7 | 0.5 |
| 16:35 | Air | 134.6 | 0.5 |
| 16:40 | Soltrol 130 | 165.9 | 0.5 |
| 16:45 | Air | 134.5 | 0.6 |
| 16:48 | Soltrol 130 | 163.3 | 1.0 |
| 16:53 | Air | 135.4 | 0.5 |
| 17:02 | Brine 20 g/l | 193.8 | 0.6 |

While the invention has been described as used on a relatively small pipeline, it can be used on any size closed vessel or pipeline to identify the fluid within the vessel or pipeline. Of course, as larger vessels or pipelines are used, it will be necessary to use larger transducers and larger sources for exciting them. In any case, the resonant frequency of the transducers should be in the ultrasonic range, preferably between 0.2 and 10 MHz.

In addition, using a constant rate pump, one can detect very small volumes of fluid on the order of 0.05 cc using these small diameter pipes. This arrangement provides an accurate flow measuring system for small quantities of fluids.

I claim as my invention:

1. An ultrasonic apparatus for identifying the fluid in a vessel comprising:
    a pair of transducers mounted to transmit ultrasonic energy through said fluid and receive the ultrasonic energy after it has passed through the fluid;
    amplifier means, said transducers being coupled in series in the feedback circuit of said amplifier means, said amplifier means including adjustable elements for adjusting the impedance of the amplifier means to cause it to resonate; and,
    a measuring circit, said measuring circuit including means for producing a repeatable ramp voltage and measuring the time required to cause an amplifier circuit to resonate using said preset ramp voltage to adjust the impedence of the amplifier.

2. The apparatus of claim 1 and in addition a clock circuit, said clock circuit producing a measurement interval, said clock circuit in addition initiating the production of said ramp voltage at the start of said measuring interval, and means for counting said clock pulses between the start of resonance of said circuit means and the end of said measuring interval.

3. The apparatus of claim 2 and in addition the output voltage of said circuit means being compared to a reference voltage to produce a control signal when said circuit voltage exceeds said reference voltage, said control signal being used to initiate the counting of said clock pulses.

4. The apparatus of claim 3 wherein said control voltage sets a flip-flop circuit to initiate counting of said clock pulses, said flip-flop being reset by the end of said measuring interval.

5. The apparatus of claim 2 wherein the total count of said clock pulses is visually displayed.

6. The apparatus of claim 2 wherein the total count of said clock pulses is correlated with the fluid in said vessel.

* * * * *